(12) United States Patent
Corbett

(10) Patent No.: US 8,675,197 B2
(45) Date of Patent: Mar. 18, 2014

(54) PARTICLE CHARACTERIZATION

(75) Inventor: Jason Cecil William Corbett, Hereford (GB)

(73) Assignee: Malvern Instruments, Ltd., Malvern (GB)

( * ) Notice: Subject to any disclaimer, the term of this patent is extended or adjusted under 35 U.S.C. 154(b) by 0 days.

(21) Appl. No.: 12/717,906

(22) Filed: Mar. 4, 2010

(65) Prior Publication Data
US 2010/0253945 A1 Oct. 7, 2010

Related U.S. Application Data

(63) Continuation of application No. PCT/GB2010/050382, filed on Mar. 4, 2010, and a continuation of application No. PCT/GB2010/050383, filed on Mar. 4, 2010.

(60) Provisional application No. 61/209,139, filed on Mar. 4, 2009, provisional application No. 61/209,138, filed on Mar. 4, 2009.

(51) Int. Cl.
*G01N 21/01* (2006.01)
*G01N 21/47* (2006.01)

(52) U.S. Cl.
USPC .......................................... 356/338; 356/246

(58) Field of Classification Search
USPC .................................. 356/335–343, 244–246
See application file for complete search history.

(56) References Cited

U.S. PATENT DOCUMENTS

| | | | |
|---|---|---|---|
| 4,521,521 A | | 6/1985 | Abbott |
| 4,573,796 A | * | 3/1986 | Martin et al. .................. 356/318 |
| 4,576,477 A | * | 3/1986 | Corbet et al. .................... 356/39 |
| 4,975,237 A | | 12/1990 | Watling |
| 5,040,890 A | * | 8/1991 | North, Jr. ......................... 356/72 |
| 5,434,667 A | | 7/1995 | Hutchins |
| 5,572,321 A | | 11/1996 | Pinier |
| 5,776,078 A | | 7/1998 | Wardlaw |
| 5,963,335 A | * | 10/1999 | Boutelle ........................ 356/433 |
| 6,016,195 A | | 1/2000 | Peters |
| 6,052,186 A | | 4/2000 | Tsai |
| 6,346,421 B1 | * | 2/2002 | Anderson et al. .............. 436/177 |
| 6,473,171 B1 | | 10/2002 | Buttry |
| 6,714,299 B2 | | 3/2004 | Peterson |
| 6,781,690 B2 | | 8/2004 | Armstrong |
| 6,809,826 B2 | | 10/2004 | Roberson |
| 6,809,828 B2 | | 10/2004 | Bornhop |
| 7,061,605 B2 | | 6/2006 | Lemmo |
| 7,605,919 B2 | | 10/2009 | Oma |
| 2002/0028434 A1 | * | 3/2002 | Goix et al. ......................... 435/4 |
| 2002/0154299 A1 | | 10/2002 | Robertson |
| 2004/0161368 A1 | | 8/2004 | Holtlund |
| 2006/0077390 A1 | | 4/2006 | Kralik |
| 2006/0103849 A1 | | 5/2006 | Ji |
| 2006/0109468 A1 | | 5/2006 | Evans |
| 2006/0110818 A1 | | 5/2006 | Hill |
| 2007/0224087 A1 | | 9/2007 | Ding |
| 2008/0002181 A1 | | 1/2008 | Robertson |

(Continued)

*Primary Examiner* — Hoa Pham
(74) *Attorney, Agent, or Firm* — Kristofer E. Elbing

(57) ABSTRACT

In one general aspect, a method of measuring characteristics of particles in a liquid sample is disclosed. The method includes suspending the liquid sample in a tube. The suspended liquid sample is illuminated along an illumination axis, and at least a portion of the light is detected along a first detection axis after it is scattered by the particles in the suspended liquid sample. The illumination axis and the detection axis are oriented at an angle with respect to each other.

44 Claims, 7 Drawing Sheets

(56) References Cited

U.S. PATENT DOCUMENTS

| | | | |
|---|---|---|---|
| 2008/0108146 A1 | 5/2008 | Jiang | |
| 2008/0221812 A1* | 9/2008 | Pittaro et al. | 702/66 |
| 2008/0221814 A1* | 9/2008 | Trainer | 702/70 |
| 2009/0147253 A1 | 6/2009 | Hartman | |
| 2010/0253945 A1 | 10/2010 | Corbett | |
| 2010/0277742 A1 | 11/2010 | McMillan | |
| 2011/0157586 A1 | 6/2011 | McNeil-Watson | |
| 2012/0073972 A1 | 3/2012 | Watson | |

* cited by examiner

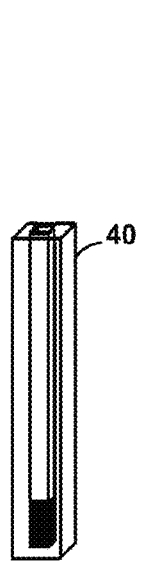 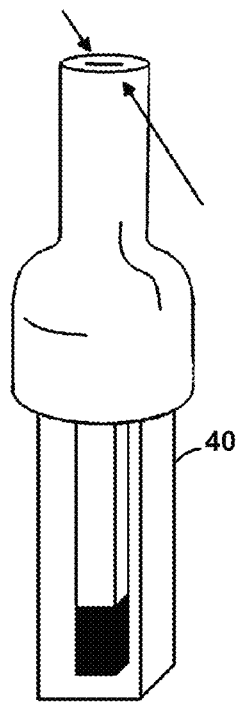 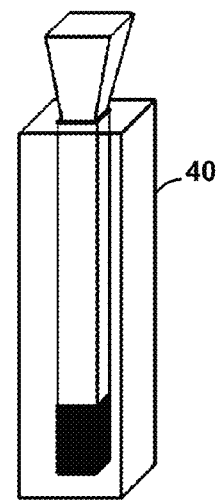 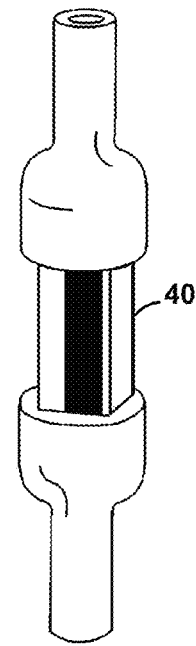
FIG. 5A  FIG. 5B  FIG. 5C  FIG. 5D
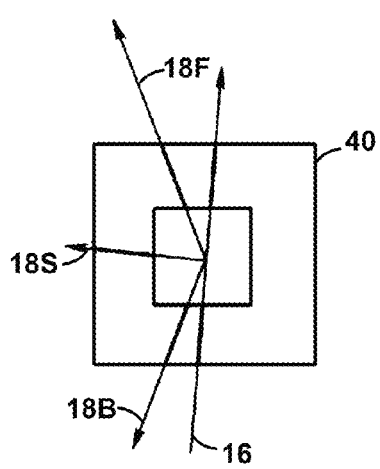 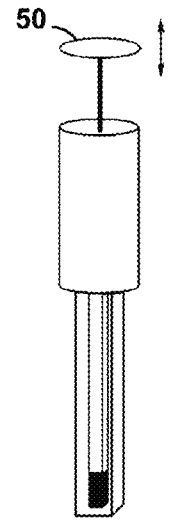 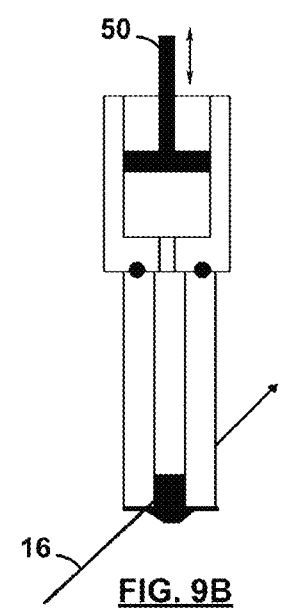
FIG. 6  FIG. 9A  FIG. 9B

PARTICLE CHARACTERIZATION

CROSS-REFERENCE TO RELATED APPLICATIONS

This application claims the benefit under 35 U.S.C. 119(e) of U.S. provisional application Ser. No. 61/209,139, filed Mar. 4, 2009 and provisional application Ser. No. 61/209,138, filed Mar. 4, 2009, and it is a continuation of PCT application number PCT/GB2010/050382, filed Mar. 4, 2010 and PCT application number PCT/GB2010/050383, filed Mar. 4, 2010. It is also related to U.S. nonprovisional application Ser. No. 12/717,900 entitled PARTICLE CHARACTERIZATION, filed today. All of these related applications are herein incorporated by reference.

FIELD OF THE INVENTION

This invention relates to methods and apparatus for detecting characteristics of particles suspended in a liquid sample, such as through the use of Static Light Scattering (SLS) and/or Dynamic Light Scattering (DLS) measurements.

BACKGROUND OF THE INVENTION

SLS and DLS measurements are typically performed using cuvettes with high-quality optical surfaces, which can be glass, in order to reduce scattering from static surfaces. These can be relatively expensive, and they can use a relatively large amount of sample material. It is also difficult to clean off residue from some types of samples, such as proteins.

SUMMARY OF THE INVENTION

In one general aspect, the invention features a method of measuring characteristics of particles in a liquid sample that includes suspending the liquid sample in a tube. The suspended liquid sample is illuminated along an illumination axis, and at least a portion of the light is detected along a first detection axis after it is scattered by the particles in the suspended liquid sample. The illumination axis and the detection axis are oriented at an angle with respect to each other.

In preferred embodiments, the liquid sample can be suspended in a tube with a removable cover. The liquid sample can be suspended in the tube by atmospheric pressure. The liquid sample can be suspended in the tube by a sealed upper surface hydraulically connected to the cavity. The sealed upper surface can be a surface of a piston. The liquid sample can be suspended by a pumping action. The method can further include steps of storing capillary tubing with the instrument and cutting the tube from the stored capillary tubing before the step of suspending the sample in the tube. The method can further include the step of cutting the tube from a length of capillary tubing before the step of suspending, with a same user performing both the step of cutting and the step of suspending. The step of providing can provide a capillary tube that is made of glass. The step of providing can provide a capillary tube that is made of plastic. The step of introducing the sample can introduce less than about 50 µl of liquid into the tube. The step of introducing the sample can introduce less than about 10 µl of liquid into the tube. The step of introducing the sample can introduce less than about 1 µl of liquid into the tube. The method can further include the step of disposing of the tube, and repeating the steps of receiving, suspending, illuminating, detecting, and disposing for further samples with new tubes for each of the further samples. The step of disposing can dispose of the tube and the sample at the same time. The method can further include the step of removing the sample from the tube before the step of disposing of the tube. The method can further include the step of causing the liquid sample to flow through the tube to a detection position before the step of detecting. The method can further include further steps of causing further samples to flow through the tube and further steps of detecting that each take place after one of the further steps of causing samples to flow. The step of causing the liquid to flow through the tube can be performed continuously. The method can further include further steps of causing further samples to flow through additional tubes and further steps of detecting that each take place after one of the further steps of causing samples to flow, with the steps of causing samples to flow being performed through disposable tubes, and the method can further include steps of disposing of the tubes between at least some of the steps of detecting.

In another general aspect, the invention features an instrument for measuring light scattered by particles in a liquid sample that includes a light source having an optical light output axis, a tube holder for a tube that includes means for suspending the liquid sample, positioned in the light output axis of the light source, and at least one scattered light detector, positioned to receive scattered light from the tube along an axis that is oriented at an angle with respect to the light output axis of the light source.

In preferred embodiments the instrument can further include an integral capillary cutting implement. The capillary cutting implement is positioned to allow the capillary tube to be cut while it is positioned in the holder along the light output axis of the light source. The capillary cutting implement can include a stationary blade attached to the capillary holder. The holder can be part of a removable capillary carrier that can be removed from the instrument. The capillary tube holder can be operative to hold a capillary tube that has a square cross-section. The capillary tube holder can be operative to hold a capillary tube that has a round cross-section. The method can further include a capillary tube held by the holder. The capillary tube can be made of glass. The capillary tube can be made of plastic. The capillary tube can be sealed at one or both ends. The tube holder can be operative to hold a tube that holds less than about 50 µl of liquid. The tube holder can be operative to hold a tube that holds less than about 10 µl of liquid. The tube holder can be operative to hold a tube that holds less than about 1 µl of liquid. The holder can be constructed and adapted to hold a tube that has an internal diameter of about 2 mm or less in the optical light output axis of the light source, with the internal diameter of the capillary tube constituting the means for suspending the liquid sample. The tube holder can be operative to hold a tube that is 0.5 mm in diameter or less. The apparatus can further include a pair of hydraulic fittings to hydraulically connect the tube to a process flow. The apparatus can further include at least a second scattered light detector positioned to receive scattered light from the tube along another angle with respect to the light output axis of the light source.

In a further general aspect, the invention features an instrument for measuring light scattered by particles in a liquid sample that includes a light source having an optical light output axis, a capillary tube holder for a capillary tube positioned in the light output axis of the light source, wherein the holder is constructed and adapted to hold a capillary tube that has an internal diameter of about 2 mm or less in the optical light output axis of the light source, and at least one scattered light detector, positioned to receive scattered light from the capillary tube along an axis that is oriented at an angle with respect to the light output axis of the light source.

In another general aspect, the invention features a method of measuring scattered light from particles in a liquid sample that includes receiving a new length of capillary tube, introducing the sample into the length of capillary tube, illuminating the sample in the capillary tube, detecting at least a portion of the light after it is scattered by the particles in the sample, disposing of the capillary tube, and repeating the steps of receiving, introducing, illuminating, detecting, and disposing for further samples with new tubes for each of the further samples.

In a further general aspect, the invention features a method of measuring characteristics of particles in a liquid sample, that includes supporting the liquid sample by atmospheric pressure, illuminating the supported liquid sample along an illumination axis, and detecting at least a portion of the light along a first detection axis after it is scattered by the particles in the supported liquid sample, wherein the illumination axis and the detection axis are oriented at an angle with respect to each other. In preferred embodiments the liquid sample can be supported in a capillary tube with a removable cover.

In another general aspect, the invention features an instrument for measuring characteristics of particles in a liquid sample that includes a cavity for holding the liquid sample, a sealed upper surface hydraulically connected to the cavity, a light source having an illumination axis directed through the cavity, and at least one scattered light detector positioned to receive light scattered by the particles in the liquid sample along a first detection axis that is oriented at an angle with respect to the light output axis of the light source when the liquid sample is trapped in the cavity. In preferred embodiments the cavity can be defined by a tube. The sealed upper surface can be provided by a removable cover.

In a further general aspect, the invention features a method of measuring characteristics of particles in a liquid sample that includes causing the liquid sample to flow through a capillary tube, illuminating the flowing liquid sample through a wall of the capillary tube along an illumination axis, and detecting at least a portion of the light along a first detection axis after it is scattered by the particles in the flowing liquid sample, wherein the illumination axis and the detection axis are oriented at an angle with respect to each other.

In preferred embodiments the method can further include further steps of causing the sample to flow through the capillary tubes and further steps of detecting that each take place after one of the further steps of causing the sample to flow. The steps of causing the liquid to flow through the capillary tube can be performed through disposable capillaries and the method can further include steps of disposing of the disposable capillaries between at least some of the measurements. The step of causing the liquid to flow through the capillary tube can be performed continuously.

In another general aspect, the invention features an instrument for measuring characteristics of particles in a liquid sample that includes an open length of capillary tube having a first open end and a second open end, an input hydraulic connection between the first end and a process flow output, an output hydraulic connection between the second end and a process flow input, a light source having an illumination axis directed through the capillary tube, and at least one scattered light detector positioned to receive light scattered by the particles in the liquid sample along a first detection axis that is oriented at an angle with respect to the light output axis of the light source when the liquid sample is trapped in the cavity.

In a further general aspect, the invention features a method of measuring characteristics of particles in a liquid sample that includes supporting the liquid sample by surface tension and illuminating the supported liquid sample along an illumination axis with spatially coherent light so as to cause the coherent light to be scattered across a scattering zone. At least a portion of the scattered light is detected along a first predetermined scattering detection axis after it is scattered by the particles in the supported liquid sample. The illumination axis and the detection axis are oriented at an angle with respect to each other that allows substantially all of the light scattered at that angle across the scattering zone to be detected.

In preferred embodiments the method can further include the step of deriving a dynamic light scattering measurement for a predetermined angular resolution from results of the step of detecting. The method can further include the step of deriving a static light scattering measurement for a predetermined angular resolution from results of the step of detecting. The liquid sample can be supported in a gap defined by two wicking surfaces. The step of illuminating can be performed through a supporting surface on the sample. The step of illuminating can be performed through an unsupported surface on the sample. The step of detecting can be performed through a supporting surface on the sample. The step of detecting can be performed through an unsupported surface on the sample. The method can include further steps of detecting along further detection axes that are oriented at further angles with respect to the illumination axis. The step of supporting can include supporting the sample in a sample carrier, with the method further including the step of positioning the sample carrier so that the first optical axis intersects the sample. The step of detecting can detect backscattered light. The step of illuminating can illuminate the trapped liquid sample with at least partially coherent light. The step of illuminating can illuminate the trapped liquid sample with coherent light. The step of detecting can detect time-averaged scattered light for a sample. The step of detecting can detect time-dependent scattered light for a sample.

In another general aspect, the invention features an instrument for measuring characteristics of particles in a liquid sample that includes one or more wicking surfaces and a spatially coherent light source having an illumination axis directed proximate the wicking surfaces so as to cause coherent light from the source to be scattered across a scattering zone. At least one spatially coherent scattered light detector is positioned to receive light scattered by the particles in the liquid sample along a first predetermined scattering detection axis that is oriented at an angle with respect to the illumination axis of the light source when the liquid sample is trapped by the wicking surfaces. The angle between the predetermined scattering detection axis and the illumination axis allows the detector to detect substantially all of the coherent light scattered at that angle across the scattering zone.

In preferred embodiments one or more of the wicking surfaces are each part of one or more transparent optical parts. The source can be positioned to direct light through a first of the wicking surfaces. The detector can be positioned to receive scattered light through a first of the wicking surfaces. The source can be positioned to direct light toward a position on a surface of the trapped sample that does not touch either of the wicking surfaces. The detector can be positioned to receive scattered light from a position on a surface of the trapped sample that does not touch either of the wicking surfaces. The detector can be positioned to receive backscattered light from the sample. The first wicking surface can be part of a first transparent optical part and the second wicking surface can be part of a second transparent optical part that is separate from the first transparent optical part. The apparatus can further include a supporting body positioned to hold the wicking surfaces in place. The supporting body can be part of a removable sample carrier that can be removed from the instrument. There can be four wicking surfaces for a single sample. All four of the wicking surfaces can each be part of a transparent optical part. The illumination axis of the light source can pass through the sample without passing through any of the wicking surfaces. A gap can defined by the wicking surfaces can be sized to hold an aqueous sample between the first wicking surface and the second wicking surface by surface tension. The first and second wicking surfaces can be parallel to each other. The first and second wicking surfaces can be positioned at an angle, which can be equal to a scattering angle between the illumination axis of the light source and the detection axis of the detector. The light source can be a laser.

In a further general aspect, the invention features a method of measuring characteristics of particles in a liquid sample that includes supporting the liquid sample by surface tension over at least one supported surface, illuminating the supported liquid sample through the supported surface of the liquid along an illumination axis, and detecting at least a portion of the light along a first scattering detection axis after it is scattered by the particles in the supported liquid sample, wherein the illumination axis and the detection axis are oriented at an angle with respect to each other.

In another general aspect, the invention features an instrument for measuring characteristics of particles in a liquid sample that includes one or more wicking surfaces, a light source having an illumination axis directed through at least one of the wicking surfaces, and at least one scattered light detector positioned to receive light scattered by the particles in the liquid sample along a first scattering detection axis that is oriented at an angle with respect to the illumination axis of the light source when the liquid sample is trapped by the wicking surfaces.

In a further general aspect, the invention features a method of measuring characteristics of particles in a liquid sample that includes supporting the liquid sample by surface tension over at least one supported surface, illuminating the supported liquid sample along an illumination axis, and detecting at least a portion of the light through an unsupported surface of the liquid along a first scattering detection axis after it is scattered by the particles in the supported liquid sample, wherein the illumination axis and the detection axis are oriented at an angle with respect to each other.

In another general aspect, the invention features an instrument for measuring characteristics of particles in a liquid sample that includes one or more wicking surfaces, a light source having an illumination axis directed proximate the wicking surfaces, and at least one scattered light detector positioned to receive light scattered by the particles in the liquid sample through a surface that is unsupported by the wicking surfaces along a first scattering detection axis that is oriented at an angle with respect to the illumination axis of the light source when the liquid sample is trapped by the wicking surfaces.

Measurement systems according to the invention can perform scattering measurements quickly and efficiently. By holding a small drop of sample fluid in the path of an incident beam, scattering measurements for one or more scattering modes can be performed on a very small sample. The components used to hold the samples can then be disposed of or easily cleaned. The use of separate wicking surfaces to support samples allows for easy cleaning of surfaces, and these may even be provided on a disposable optical element. Capillary tubes can hold a very small amount of liquid for scattering measurements and then be discarded.

BRIEF DESCRIPTION OF THE DRAWING

FIG. 5A is a diagram showing a sample trapped by surface tension within a capillary;

FIG. 5B is a diagram of a sample trapped by atmospheric pressure via a pinched top;

FIG. 5C is a diagram of a sample trapped by atmospheric pressure via a sealed top;

FIG. 5D is a diagram of a sample trapped within a capillary as part of a flow path;

FIG. 6 is a cross-sectional diagram showing an optical geometry for a capillary tube;

FIGS. 9A and 9B show a piston that may be used to draw a precise amount of a liquid sample into a capillary tube, hold it (if necessary), and then expel it (if necessary).

DETAILED DESCRIPTION OF AN ILLUSTRATIVE EMBODIMENT

Referring to FIG. 1, an illustrative embodiment of a particle characteristics measuring instrument can perform trapped droplet sample presentation for static and dynamic light scattering instruments in forward, side and backscatter.

S/DLS measurements can require very small sample volumes to reduce costs. Further, S/DLS measurements require very high optical quality surfaces in order to reduce scattering from static surfaces, precluding the use of low optical quality disposable plastic cells. Further still, proteins, for example, are often very difficult to clean from glass cuvettes that are typically quite deep and prevent the entry of mechanical cleaning devices, such as brushes.

In instruments according to the invention, however, a sample droplet 10 is placed on a lower optical surface 12—see FIG. 1(*a*). In one embodiment, the incident light beam 16 and detected light beam 18 intersect within the droplet, with the droplet in contact only with the lower surface. In another embodiment the upper optical surface 14 is moved down until it makes contact with the sample—FIG. 1(*b,c,d*). The sample droplet wicks onto the upper surface, whilst remaining attached to the lower surface. The sample is trapped by surface tension. The upper surface is then drawn up to create a sample bridge within which the incident and detection beams can intersect. The distance between the optical surfaces would typically be of the order of 1-2 mm. The position of the crossover (intersection of incident and detected light beams) within the trapped droplet can be set via separate optics: i.e. independently of the position of the optical surfaces. e.g. in backscatter via NIBS technology (described in U.S. Pat. No. 6,016,195 which is herein incorporated by reference)—see FIG. 3 for example. The sample may also be trapped between more than two surfaces e.g. see FIG. 2 (12, 14, 22, 24), and opposing surfaces may be non-parallel—FIG. 1(d). The surfaces exposed to the sample may be any shape deemed convenient and/or necessary for efficient trapping of the sample via surface tension and/or optical deviation and focusing of the incident and detected beams.

Figure 1A:
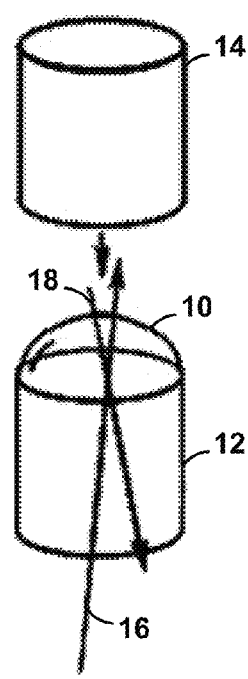
FIG. 1 is a series of diagrams illustrating the use of optical components to trap sample droplets in various static and dynamic light scattering measurement configurations with one or two-face optical layouts.
Figure 1B:
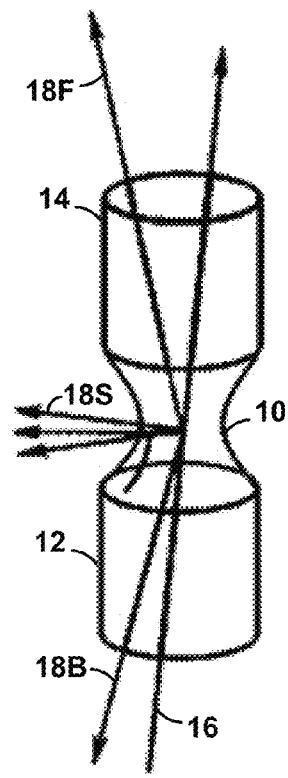
Figure 1C:
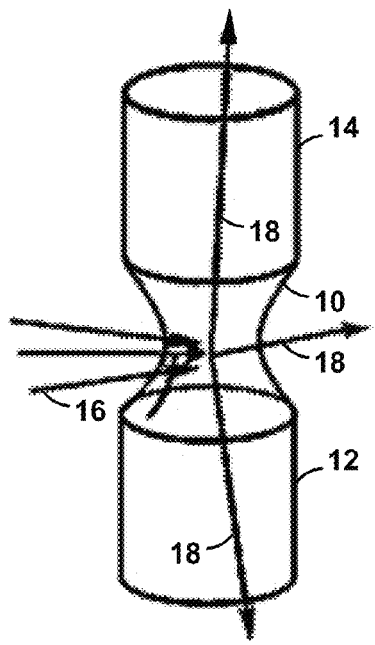
Figure 1D:
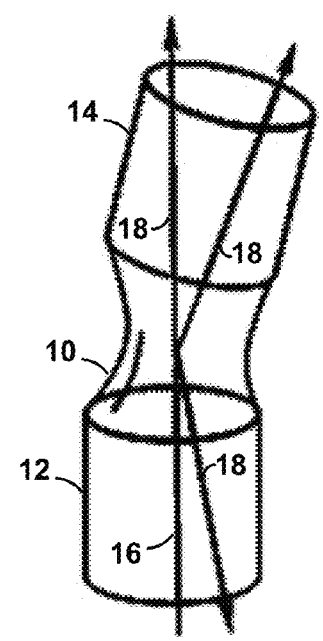
Figure 2:
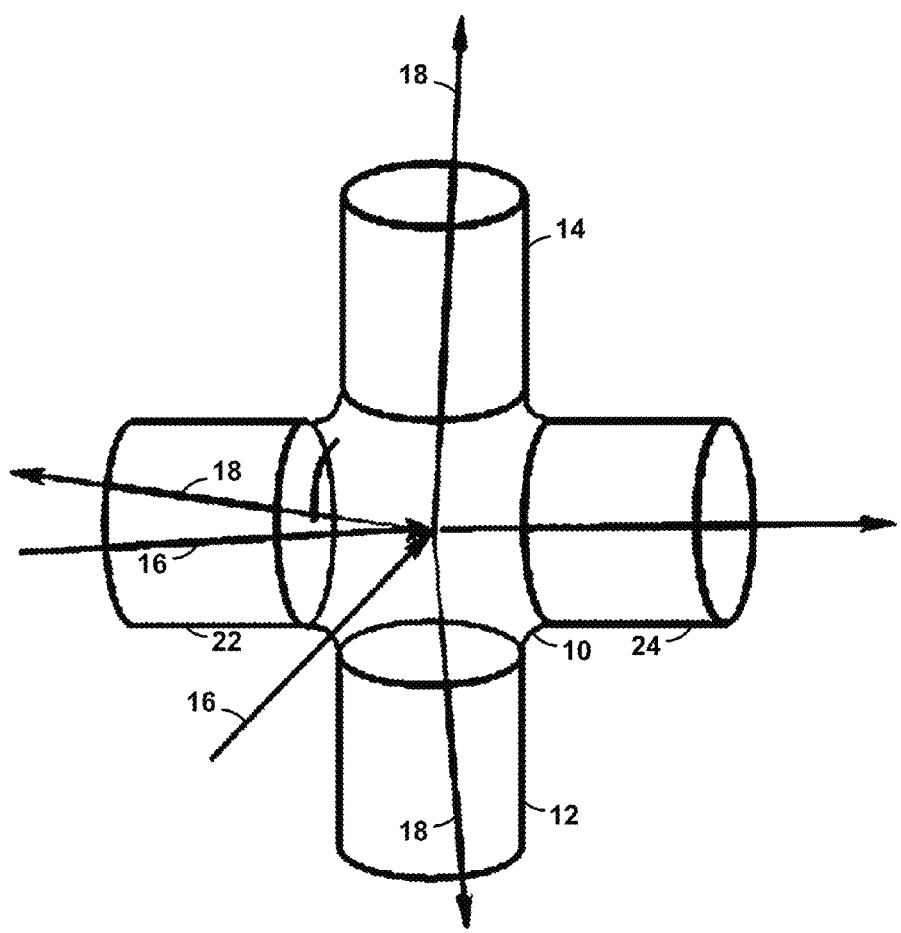
FIG. 2 is diagram illustrating the use of optical components to trap a sample droplet in a dynamic light scattering measurement configuration with a multiple-face optical layout.

In FIG. 1(b), the light enters the droplet 10 through one of the optical surfaces at some appropriate, well-defined angle and is detected in either forward 18F or backscatter 18B (again at some appropriate angle) through the optical surfaces or at a higher angle (typically, but not exclusively, 90 degrees to the input beam 18S) through the droplet side. In FIG. 1(c) the beam enters through the side of the droplet and is detected through either or both of upper and lower optical surfaces or through the droplet side.

In all proposed cases, FIG. 1(a)-(d), all optical beams (incident and detected) should have a well defined angle with respect to each other and should be pseudo-monochromatic, with centre wavelength, $\lambda$. The ISO standard for DLS (ISO 22412) states that the reported size should be $+/-2\%$ of the validated value of a standard sample. The Cumulants analysis is the standard basic reduction and it equates the measured quantity, g1, the correlation function, to the fit, $$g^1(q, \tau) = \exp(-\Gamma\tau)\left(1 + \frac{\mu^2}{2!}\tau^2 + \ldots\right) \quad (1)$$

$\Gamma$, is related to the diffusion coefficient, D via the q vector by $$\Gamma = q^2 D \quad (2)$$

where $$q = \frac{4\pi n}{\lambda}\sin\left(\frac{\theta}{2}\right) \quad (3)$$

In which $\theta$ is the angle between the incident and detected beams. n, is the refractive index of the dispersant in which the particles are dispersed. The particle radius, r, is then related to the diffusion coefficient via the Stokes-Einstein relation $$D = \frac{k_B T}{6\pi \eta r} \quad (4)$$

Where, $k_B$ is the Boltzmann constant and T is the temperature. Via Eq. (2), $q^2$ should be defined to $<2\%$ to meet the ISO standard and thence $\theta$ to within $1.414=\sqrt{2}\leq 1.5\%$. We should also, then, define $\lambda$ to $<2\%$ for DLS. The requirements of SLS are a subset of $\theta+/-1.5\%$ and $\lambda+/-2\%$.

Figure 3C:
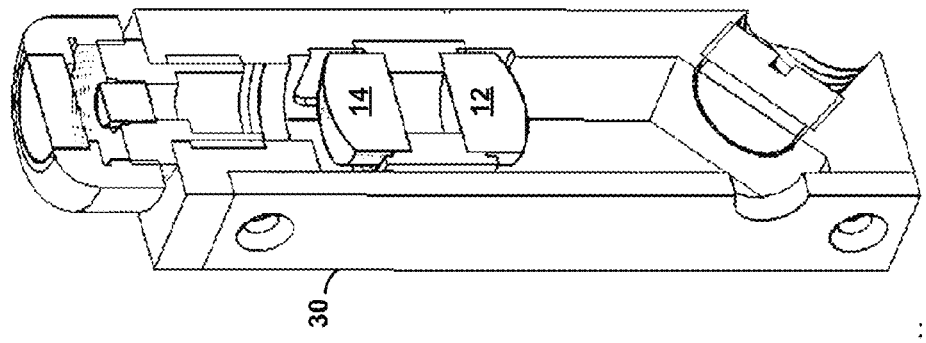
FIG. 3C is a cutaway view of the holder of FIG. 3A.
Figure 3B:
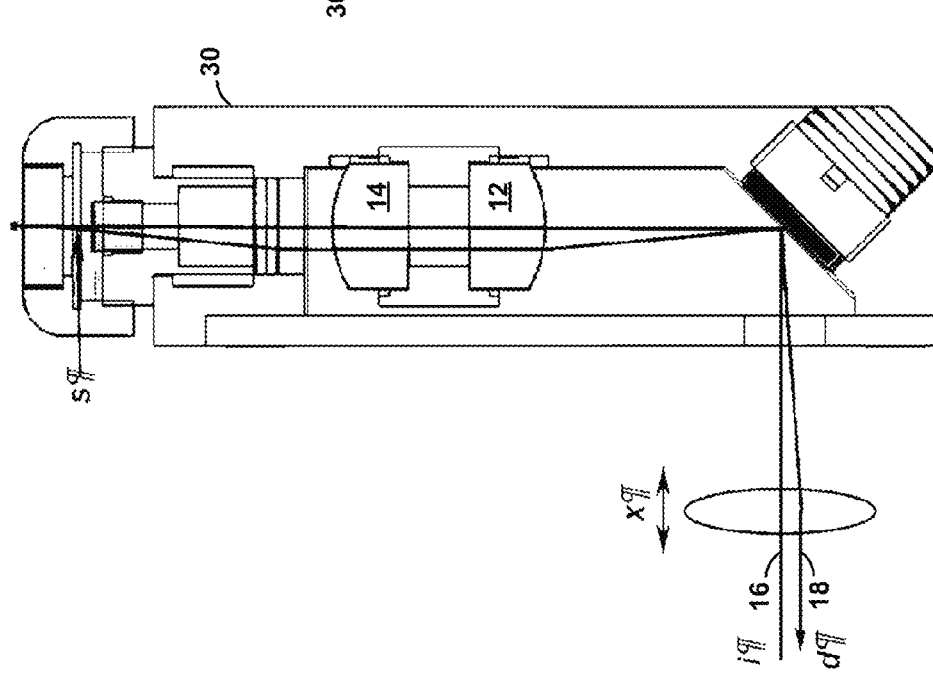
FIG. 3B is a cross-sectional view of the holder of FIG. 3A that uses NIBS to position crossover of an incident beam.
Figure 3A:
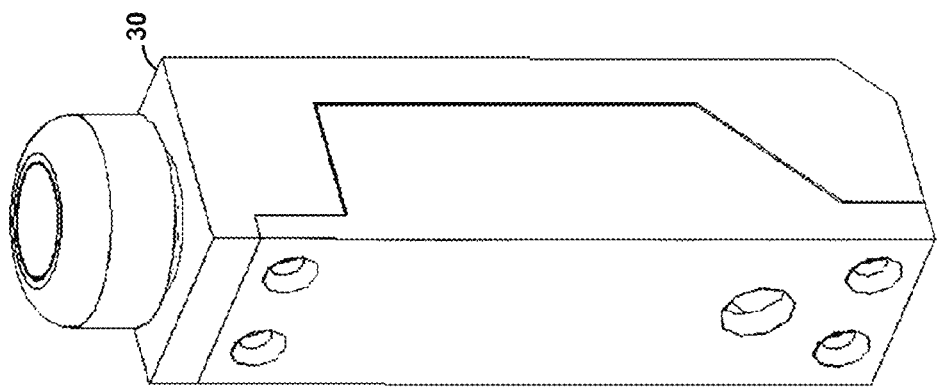
FIG. 3A is an isometric projection of a holder for use with light scattering measurement configurations such as those shown in FIG. 1.
Figure 4:
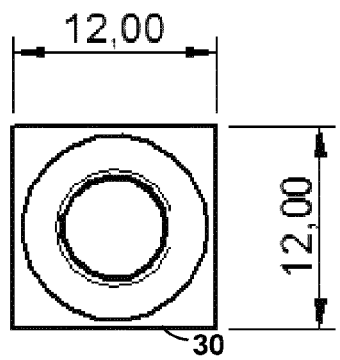
FIG. 4 is a three-view drawing of the holder showing illustrative overall dimensions to fit in commonly found cuvette holders.
Figure 4:
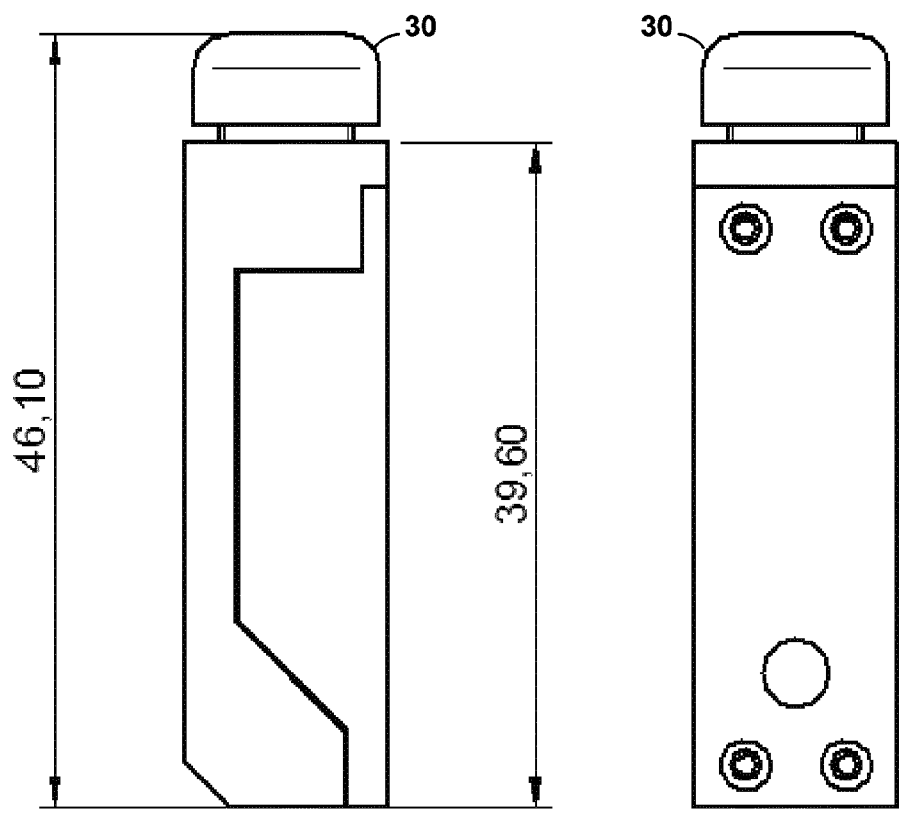

One embodiment of the scheme is shown in FIG. 3. The entire apparatus can fit inside the cuvette holder 30 of a Zetasizer Nano particle characterization instrument underneath the thermal cap in order to provide degree of thermal control appropriate to S/DLS. The Zetasizer Nano particle characterization instrument is available from Malvern Instruments of Malvern, UK, and is discussed in more detail in U.S. application Nos. 61/206,688 and 61/195,647, which are herein incorporated by reference.

Once measured the sample can be re-pipetted for further use and any material left on the optical surfaces removed with easy access.

Another approach involves a semi disposable sample presentation scheme for the measurement of dynamic and static light scattering for size and molecular weight determination in forward, side and backscatter. This scheme can allow for presentation of very small sample volumes to D/SLS instruments in an easy to use and semi-disposable format.

Good optical quality glass or plastic capillary tubing is available relatively cheaply now and the following scheme is proposed—FIG. 5. A length of capillary 40 is held in place (as required by the optical geometry of the instrument) and the tube filled from either end by attached tube or a pipette. The sample is retained by one of three mechanisms. In the first instance, the capillary is small enough to trap the sample by surface tension with the other end of the capillary left open to atmosphere—FIG. 5(a)—for example. In the second instance, the top of the capillary is sealed by some means—FIG. 5(b) and FIG. 5(c) for example—so that the sample is trapped within the capillary by atmospheric pressure at the capillary bottom (sample end in FIG. 5). In the third instance, the capillary forms part of a flow circuit—FIG. 5(d) for example.

The incident light beam may enter the sample through any side face of the capillary—FIG. 6. One or more detection beams may also exit the cell through any or all of the side faces of the capillary.

Figure 7A:
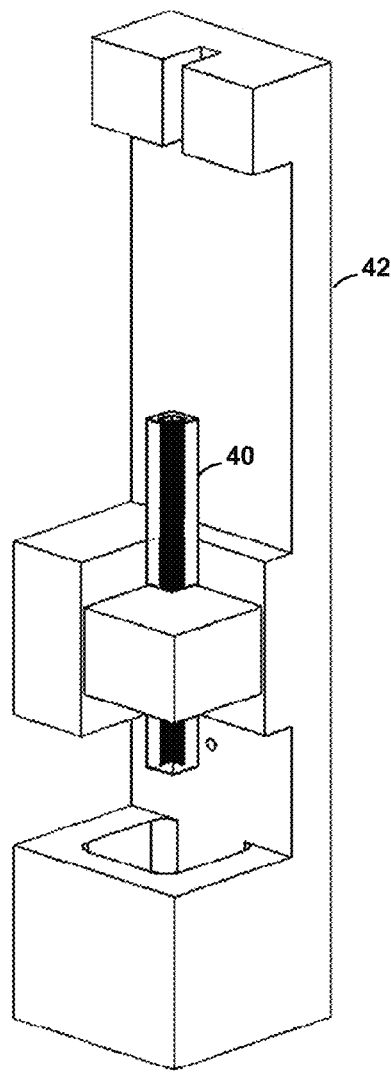
FIG. 7A is an illustrative implementation of a capillary carrier including a slot at the top to trap and seal a flexible tube (attached to the top end of the capillary) for atmospheric trapping of sample as show in FIG. 5B.
Figure 7B:
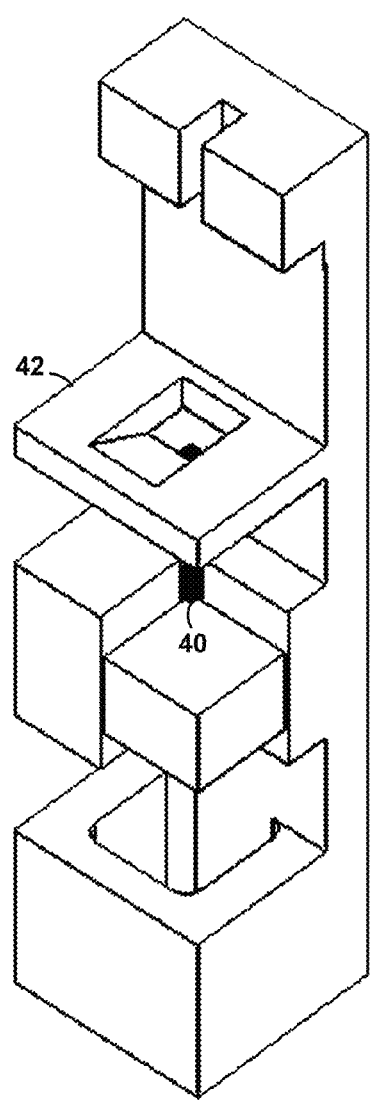
FIG. 7B is an illustrative implementation of a capillary carrier including a capillary cutter 44.
Figure 8:
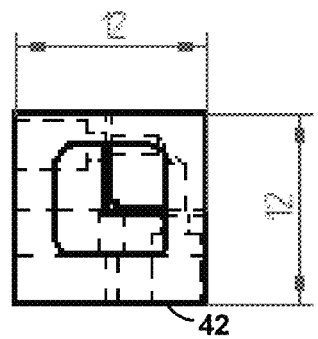
FIG. 8 is three-view drawing of the capillary carrier of FIG. 7A holder showing illustrative overall dimensions to fit in commonly found cuvette holders.
Figure 8:
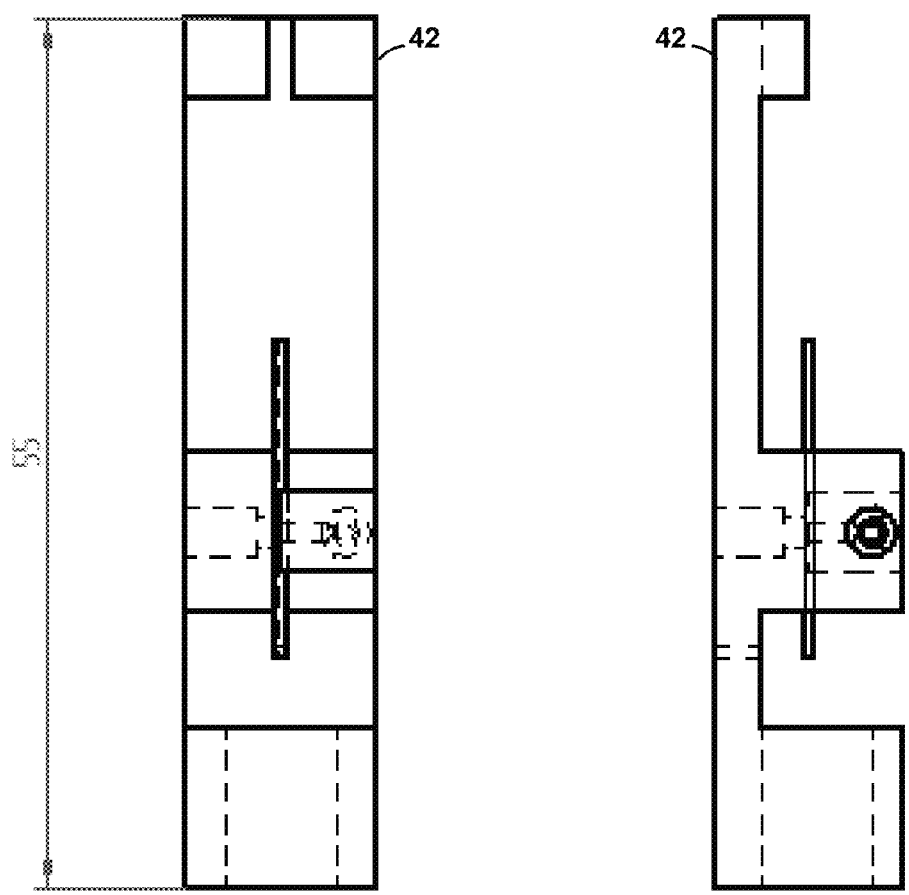

The capillary 40 is held in place by a carrier 42—FIG. 7, which is then located into the instrument. The dimensions of the carrier match those of a standard cuvette, such that it enables use in an instrument in which standard cuvettes are used. Typical dimensions of such a carrier are shown in FIG. 8. A device for cutting the capillary to length whilst fitting into the carrier is also proposed, an example of which is shown in FIG. 7(b). Once in place the sample is pippetted into the bottom of the capillary as shown in FIG. 5—the large hole in the base of the carrier—FIG. 7—is included for this purpose. Once the measurement is complete the sample may then be re-pippetted out of the capillary for further analysis.

If the capillary becomes dirty in use it may be cheaply disposed of and a new one fitted for further measurements. Capillaries of 0.5 mm internal dimensions and smaller are readily available thereby allowing convenient, semi-disposable measurement volumes of 10's to 100's of nanolitres for the first time.

Referring to FIG. 9, a piston 50 or other pumping mechanism may be provided to draw a precise amount of a liquid sample into a capillary tube, hold it (if necessary), and then expel it (if necessary). The use of a piston can allow even a very small drop to be positioned precisely within a capillary tube in the path of an incident beam. The piston may be advanced by a screw, a motor, or another suitable mechanism.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

What is claimed is:

1. A method of measuring characteristics of particles suspended in a liquid sample, comprising:
   suspending the liquid sample, which includes the suspended particles, in a tube,
   placing the tube in an S/DLS instrument,
   illuminating the suspended particles in the suspended liquid sample along an illumination axis, and
   detecting at least a portion of the light along a first detection axis after it is scattered by the suspended particles in the suspended liquid sample to obtain an S/DLS measurement, wherein the illumination axis and the detection axis are oriented at an angle with respect to each other.

2. The method of claim 1 wherein the liquid sample is suspended in a tube with a removable cover.

3. The method of claim 1 wherein the liquid sample is suspended in the tube by atmospheric pressure.

4. The method of claim 1 wherein the liquid sample is suspended in the tube by a sealed upper surface hydraulically connected to the cavity.

5. The method of claim 4 wherein the sealed upper surface is a surface of a piston.

6. The method of claim 1 wherein the liquid sample is suspended by a pumping action.

7. The method of claim 1 further including steps of storing capillary tubing with the instrument and cutting the tube from the stored capillary tubing before the step of suspending the sample in the tube.

8. The method of claim 1 further including the step of cutting the tube from a length of capillary tubing before the step of suspending, wherein a same user performs both the step of cutting and the step of suspending.

9. The method of claim 1 wherein the step of providing provides a capillary tube that is made of glass.

10. The method of claim 1 wherein the step of providing provides a capillary tube that is made of plastic.

11. The method of claim 1 wherein the step of introducing the sample introduces less than about 50 µl of liquid into the tube.

12. The method of claim 1 wherein the step of introducing the sample introduces less than about 10 µl of liquid into the tube.

13. The method of claim 1 wherein the step of introducing the sample introduces less than about 1 µl of liquid into the tube.

14. The method of claim 1 further including the step of disposing of the tube, and repeating the steps of suspending, placing, illuminating, detecting, and disposing for further samples with new tubes for each of the further samples.

15. The method of claim 14 wherein the step of disposing disposes of the tube and the sample at the same time.

16. The method of claim 14 further including the step of removing the sample from the tube before the step of disposing of the tube.

17. The method of claim 1 further including the step of causing the liquid sample to flow through the tube to a detection position before the step of detecting.

18. The method of claim 17 further including further steps of causing further samples to flow through the tube and further steps of detecting that each take place after one of the further steps of causing samples to flow.

19. The method of claim 18 wherein the step of causing the liquid to flow through the tube is performed continuously.

20. The method of claim 17 further including further steps of causing further samples to flow through additional tubes and further steps of detecting that each take place after one of the further steps of causing samples to flow, wherein the steps of causing samples to flow are performed through disposable tubes, and further including steps of disposing of the tubes between at least some of the steps of detecting.

21. An instrument for measuring light scattered by particles suspended in a liquid sample, comprising:
   a light source having an optical light output axis,
   a removable tube holder for a tube that includes means for suspending the liquid sample, which includes the suspended particles, positioned in the light output axis of the light source, and
   at least one scattered S/DLS light detector, positioned to receive scattered light from the suspended particles in the suspended sample in the tube along an axis that is oriented at an angle with respect to the light output axis of the light source.

22. The apparatus of claim 21 wherein the instrument further includes an integral capillary cutting implement.

23. The apparatus of claim 22 wherein the capillary cutting implement is positioned to allow the tube to be cut while it is positioned in the holder along the light output axis of the light source.

24. The apparatus of claim 23 wherein the capillary cutting implement includes a stationary blade attached to the capillary holder.

25. The apparatus of claim 21 wherein the tube holder is operative to hold a capillary tube that has a square cross-section.

26. The apparatus of claim 21 wherein the tube holder is operative to hold a capillary tube that has a round cross-section.

27. The apparatus of claim 21 further including a capillary tube held by the holder.

28. The apparatus of claim 27 wherein the capillary tube has a square cross-section.

29. The apparatus of claim 27 wherein the capillary tube is made of glass.

30. The apparatus of claim 27 wherein the capillary tube is made of plastic.

31. The apparatus of claim 27 wherein the capillary tube has a round cross-section.

32. The apparatus of claim 27 wherein the capillary tube is sealed at one or both ends.

33. The apparatus of claim 21 wherein the tube holder is operative to hold a tube that holds less than about 50 µl of liquid.

34. The apparatus of claim 21 wherein the tube holder is operative to hold a tube that holds less than about 10 µl of liquid.

35. The apparatus of claim 21 wherein the tube holder is operative to hold a tube that holds less than about 1 µl of liquid.

36. The apparatus of claim 21 wherein the holder is constructed and adapted to hold a tube that has an internal diameter of about 2 mm or less in the optical light output axis of the light source, and wherein the internal diameter of the tube constitutes the means for suspending the liquid sample.

37. The apparatus of claim 36 wherein the tube holder is operative to hold a tube that is 0.5 mm in diameter or less.

38. The apparatus of claim 21 further including a pair of hydraulic fittings to hydraulically connect the tube to a process flow.

39. The apparatus of claim 21 further including at least a second scattered light detector positioned to receive scattered light from the tube along another angle with respect to the light output axis of the light source.

40. The apparatus of claim 21 wherein the holder further includes a tube.

41. The apparatus of claim 40 wherein the tube is small enough to trap the sample by surface tension.

42. An instrument for measuring light scattered by particles suspended in a liquid sample, comprising:
- a light source having an optical light output axis,
- a removable sample carrier that includes means for suspending the liquid sample, which includes the suspended particles,
- a holder having dimensions that match the removable sample carrier and position the liquid sample in the light output axis of the light source when the removable sample carrier is inserted in the holder of the instrument, and
- at least one scattered S/DLS light detector, positioned to receive scattered light from the particles suspended in the liquid sample suspended in the sample carrier along an axis that is oriented at an angle with respect to the light output axis of the light source.

43. The apparatus of claim 42 wherein the removable sample carrier includes a tube held in a tube holder.

44. The apparatus of claim 42 wherein the removable sample carrier is the same size as a cuvette for the instrument.

\* \* \* \* \*